US011191819B2

(12) United States Patent
Sanders

(10) Patent No.: US 11,191,819 B2
(45) Date of Patent: Dec. 7, 2021

(54) SKIN THERAPEUTICS

(71) Applicant: Ira Sanders, North Bergen, NJ (US)

(72) Inventor: Ira Sanders, North Bergen, NJ (US)

(73) Assignee: Ira Sanders, North Bergen, NJ (US)

( * ) Notice: Subject to any disclaimer, the term of this patent is extended or adjusted under 35 U.S.C. 154(b) by 0 days.

(21) Appl. No.: 17/272,272

(22) PCT Filed: Aug. 28, 2019

(86) PCT No.: PCT/US2019/048655
§ 371 (c)(1),
(2) Date: Feb. 26, 2021

(87) PCT Pub. No.: WO2020/047159
PCT Pub. Date: Mar. 5, 2020

(65) Prior Publication Data

US 2021/0177947 A1 Jun. 17, 2021

Related U.S. Application Data

(60) Provisional application No. 62/918,603, filed on Feb. 6, 2019, provisional application No. 62/723,742, filed on Aug. 28, 2018.

(51) Int. Cl.

| | |
|---|---|
| ***A61K 38/48*** | (2006.01) |
| ***A61P 17/00*** | (2006.01) |
| ***A61K 9/00*** | (2006.01) |
| ***A61K 9/08*** | (2006.01) |
| ***A61K 31/137*** | (2006.01) |

(52) U.S. Cl.
CPC ........ *A61K 38/4893* (2013.01); *A61K 9/0014* (2013.01); *A61K 9/0019* (2013.01); *A61K 9/08* (2013.01); *A61K 31/137* (2013.01); *A61P 17/00* (2018.01)

(58) Field of Classification Search
None
See application file for complete search history.

(56) References Cited

U.S. PATENT DOCUMENTS

| | | | | |
|---|---|---|---|---|
| 5,670,484 | A * | 9/1997 | Binder | A61K 38/162 514/18.6 |
| 5,766,605 | A | 6/1998 | Sanders et al. | |
| 6,143,306 | A | 11/2000 | Donovan | |
| 7,226,605 | B2 | 6/2007 | Suskind et al. | |
| 7,255,865 | B2 | 8/2007 | Walker | |
| 7,288,259 | B2 | 10/2007 | Sanders et al. | |
| 7,335,367 | B2 | 2/2008 | Borodic | |
| 7,390,318 | B2 | 6/2008 | Olejnik et al. | |
| 7,429,386 | B2 | 9/2008 | First | |
| 7,445,783 | B2 | 11/2008 | Cappello | |
| 7,479,281 | B1 | 1/2009 | Walker | |
| 7,507,419 | B2 | 3/2009 | Coleman, III et al. | |
| 7,666,435 | B2 | 2/2010 | Sanders et al. | |
| 7,691,394 | B2 | 4/2010 | Borodic | |
| 7,727,537 | B2 | 6/2010 | Modi | |
| 7,824,693 | B2 | 11/2010 | Sanders | |
| 7,838,007 | B2 | 11/2010 | Brin et al. | |
| 7,879,340 | B2 | 2/2011 | Sanders | |
| 8,088,360 | B2 | 1/2012 | Sanders | |
| 8,092,781 | B2 | 1/2012 | Sanders | |
| 8,153,139 | B1 | 4/2012 | Sanders et al. | |
| 8,202,522 | B1 | 6/2012 | Sanders et al. | |
| 8,349,292 | B2 | 1/2013 | Sanders | |
| 8,846,622 | B2 | 9/2014 | Blumenfeld | |
| 9,314,513 | B2 | 4/2016 | Sanders | |
| 9,504,735 | B2 | 11/2016 | Sanders | |
| 9,579,368 | B2 | 2/2017 | Bratbak et al. | |
| 2002/0086036 | A1 | 7/2002 | Walker | |
| 2002/0094339 | A1 | 7/2002 | Brin et al. | |
| 2003/0224020 | A1 | 12/2003 | Zabudkin et al. | |
| 2004/0009180 | A1 | 1/2004 | Donovan et al. | |
| 2005/0074466 | A1 | 4/2005 | Suskind et al. | |
| 2005/0175636 | A1 | 8/2005 | Donovan | |
| 2005/0196414 | A1 | 9/2005 | Dake et al. | |
| 2005/0220820 | A1 | 10/2005 | Sanders et al. | |
| 2007/0116724 | A1 | 5/2007 | Waugh | |
| 2008/0081049 | A1 | 4/2008 | Sanders | |
| 2008/0112981 | A1 | 5/2008 | Sanders et al. | |
| 2008/0118533 | A1 | 5/2008 | Borodic | |
| 2008/0220020 | A1 | 9/2008 | Donovan | |

(Continued)

FOREIGN PATENT DOCUMENTS

| | | | |
|---|---|---|---|
| AU | 2003263860 | A1 | 3/2004 |
| AU | 2003263860 | A8 | 3/2004 |

(Continued)

OTHER PUBLICATIONS

Martin, D. et al. Exciting New Uses of Botulinum Toxin Type A. Botulinum Toxins Edited by Cohen and Ozog, Wiley Blackwell Chapter 25, pp. 329-344. May 17, 2017. (Year: 2017).*
Cao, L. et al. Long-Term Anti-Itch Effect of Botulinum Neurotoxin A is Associated with Downregulation of TRPVI and TRPA1 in the Dorsal Root Ganglia in Mice. Cellular, Molecular and Developmental Neuroscience 28(9)518-528, 2017. (Year: 2017).*
Bratbak et al., Pilot study of sphenopalatine injection of onabotulinumtoxinA for the treatment of intractable chronic cluster headache. Cephalalgia.36(6):503-509 (2016).
Bratbak et al., Pilot study of sphenopalatine injection of onabotulinumtoxinA for the treatment of intractable chronic migraine. Cephalalgia.37(4):356-364 (2017).
Dressler, Routine use of Xeomin in patients previously treated with Botox: long term results. Eur J Neurol.16 Suppl 2:2-5 (2009).
International Application No. PCT/US2019/048655 International Search Report and Written Opinion dated Dec. 20, 2019.

(Continued)

*Primary Examiner* — Ralph J Gitomer
(74) *Attorney, Agent, or Firm* — Wilson Sonsini Goodrich & Rosati

(57) ABSTRACT

Disclosed herein are methods and compositions for treatment of skin disorders and diseases using botulinum toxin targeted to nerve ganglia. It has been unexpectedly found that botulinum neurotoxin (BoNT) can decrease the severity of numerous skin disorders by application to nerve ganglia including but not limited to the parasympathetic, sympathetic, and sensory ganglia

19 Claims, No Drawings

(56) References Cited

U.S. PATENT DOCUMENTS

| | | | | |
|---|---|---|---|---|
| 2008/0220021 | A1 | 9/2008 | Modi | |
| 2008/0221524 | A1 | 9/2008 | Olejnik et al. | |
| 2009/0069359 | A1 | 3/2009 | Cappello | |
| 2010/0129449 | A1 | 5/2010 | First | |
| 2010/0272754 | A1 | 10/2010 | Walker | |
| 2010/0279945 | A1 | 11/2010 | Borodic | |
| 2012/0114697 | A1 | 5/2012 | Sanders et al. | |
| 2012/0156189 | A1* | 6/2012 | Sanders ............ | A61K 38/4893 424/94.67 |
| 2016/0206711 | A1* | 7/2016 | Sanders .................. | A61P 37/06 |

FOREIGN PATENT DOCUMENTS

| | | | |
|---|---|---|---|
| CA | 2496005 | A1 | 2/2004 |
| CA | 2451923 | C | 10/2009 |
| DE | 19852981 | A1 | 5/2000 |
| EP | 1545207 | A2 | 6/2005 |
| EP | 1545207 | A4 | 8/2006 |
| EP | 2272340 | A1 | 1/2011 |
| WO | WO-0074703 | A2 | 12/2000 |
| WO | WO-0200172 | A2 | 1/2002 |
| WO | WO-03011333 | A1 | 2/2003 |
| WO | WO-03026602 | A2 | 4/2003 |
| WO | WO-2004016763 | A2 | 2/2004 |
| WO | WO-2004016763 | A3 | 6/2004 |
| WO | WO-2006116302 | A2 | 11/2006 |
| WO | WO-2008045107 | A2 | 4/2008 |
| WO | WO-2020047158 | A1 | 3/2020 |
| WO | WO-2020047159 | A1 | 3/2020 |

OTHER PUBLICATIONS

Schiavo et al., Tetanus and botulinum-B neurotoxins block neurotransmitter release by proteolytic cleavage of synaptobrevin. Nature.359(6398):832-835 (1992).

Abstracts of the International Conference 2002: Basic and Therapeutic Aspects of Botulinum and Tetanus Toxins. New York, NY: Springer-Verlag; 2002: Hannover, Germany, Jun. 8-12. 48 pages.

Becker-Wegerich, et al. Botulinum toxin A in the therapy of mimic facial lines. Clinical and Experimental Dermatology. 2001; 26: 619-630.

Benecke et al., A new botulinum toxin type A free of complexing proteins for treatment of cervical dystonia. Neurology 64(11):1949-1951 (2005).

Braune, et al. Dose thresholds and duration of local anhidrotic effect of botulinum toxin injections measured by sudometry. Br J Dermatol. 2001; 144: 111-117.

Buehr, et al. Genesis of embryonic stem cells. Phil. Trans. R. Soc. Lond. B. 2003; 358: 1397-1402.

Calvert. Types of wrinkles, http://www.calvertcreak.com.au/skin-care-advice/what-causes-wrinkles.htm dated Aug. 4, 2008.

Carruthers. Botulinum toxin type A: history and current cosmetic use in the upper face. Seminars in Cutaneous Medicine and Surgery. 2001; 20(2): 71-84.

Carruthers, et al. Improvement of tension-type headache when treating wrinkles with botulinum toxin A injections. Headache. 1999; 39:662-665.

Chichierchio, et al. Preliminary Study in the Use of Botulinum Toxin Type A. Medicina Estetica & Cosmiatria. Dermatology Clinical Skin Comer. 1997; 3:12-15.

Chung, et al. Peptidergic innervation of the primate meibomian gland. Invest Opthalmol Vis Sci.1996;37(1): 238-245.

Definition of chalazion from CIGNA, http://www.cigna.com/healthinfo/nord702.html printed Jul. 4, 2008.

EP03788573 Supplementary European search report dated Jul. 25, 2006.

EP10011716.7 European search opinion dated Dec. 1, 2010.

Gibbins, I. Target-related patterns of co-existence of neuropeptide Y, vasoactive intestinal peptide, enkephalin and substance P in cranial parasympathetic neurons innervating the facial skin and exocrine glands of guinea pigs. Neuroscience. 1990; 38 (2): 541-560.

Ho, et al. The role of botulinum toxin A in the long-term prevention of facial wrinkles: a preliminary observational report. Otolaryngology—Head and Neck Surgery. Aug. 1997; 117(2): P161.

Kunin. The anatomy of a wrinkle. AAAskindoctor.com, 2000-2004, cited Aug. 4, 2008; http://www.aaaskindoctor.com/wrinkleanatomy.html.

Letessier. Treatment of wrinkles with botulinum toxin. J. Dermatol. Treat. 1999; 10: 31-36.

Main, et al. The human external auditory canal, secretory system—an ultrastructural study. Laryngoscope. 1976; 86(8): 1164-1176.

Muraki, et al. Hair follicle involvement in herpes zoster: pathway of viral spread from ganglia to skin. Virchows Arch. 1996; 428(4-5): 275-280.

Odo, et al. Application techniques. AGE Editoria. 2002; 48-51.

Odo, et al. Botulinum toxin type A. In: Cosmetic and Medical Aesthetics Applications: Evolution of Implants and Botulinum Toxin. 2000; 159-177.

PCT/US03/25708 International search report dated Apr. 21, 2004.

Rossetto, et al. Tetanus and botulinum neurotoxins: turning bad guys into good by research. Toxicon. 2001; 39: 27-41.

Ruocco, et al. Light and electron microscopic study of the distribution of substance P-immunoreactive fibers and neurokinin-1 receptors in the skin of the rat lowerlip. J Comp Neurol. 2001; 432 (4): 466-480.

Saltzman, M: Drug Delivery. New York, NY: Oxford University Press; 2001.

Scott, A. Botulinum toxin injection of eye muscles to correct strabismus. Trans Am Opthal Soc. 1981; 179: 734-770.

Seborrhea definition from http://medical-dictionary.thefreedictionary.com/Seborrhoeic+dermititis dated Jul. 4, 2008.

Seborrheic Blepharitis definition from http://www.mountsinaihospital.org/Patient%20Care/Patient%20Care%20Services dated Jul. 4, 2008.

Simons, et al. Sensory and autonomic innervation of the rat eyelid: neuronal origins and peptide phenotypes. J Chem Neuroanat. 1994; 7(1): 35-47.

Sposito, M. New indications for botulinum toxin type A in cosmetics: mouth and neck. Plastic and Reconstructive Surgery. 2002; 110(2): 601-613.

Thody, et al. Control and function of sebaceous glands. Physiological Reviews. 1989; 69:2: 383-416.

Toyoda, et al. Pathogenesis of acne. Med Electron Microsc. Mar. 2001; 34: 29-40.

U.S. Appl. No. 60/404,378, filed Aug. 19, 2002.

Verheyden, et al. Other noncosmetic uses of BOTOX. Dis Mon. 2002; 48(5): 357-366.

Villares, J. L-dopa, biperiden and sebum excretion in Parkinson's disease. Arq Neuropsiquatr. 1989; 47(1): 31-38. [In Spanish with English summary.].

Yosipovitch et al. Sweat secretion, stratum hydration, small nerve function and pruritus in patients with advanced chronic renal failure. Br J dermatol. 1995; 133(4): 561-564.

* cited by examiner

SKIN THERAPEUTICS

CROSS-REFERENCE

This application is a U.S. National Phase of International Application No. PCT/US2019/048655, filed on Aug. 28, 2019 which claims the benefit of U.S. Provisional Application No. 62/918,602, filed Feb. 6, 2019, and Provisional Application No. 62/723,828, filed Aug. 28, 2018, and both of which are incorporated herein by reference in their entirety.

BACKGROUND OF THE INVENTION

Acne, eczema, psoriasis, seborrhea, and rosacea are common skin disorders, effective methods for treating these disorders are lacking. A variety of topical treatments are available, including treatment with botulinum toxin, but their efficacy is limited.

SUMMARY OF THE INVENTION

Disclosed herein are methods and compositions for treating skin disorders comprising applying a therapeutically effective amount of botulinum neurotoxin to nerve ganglia. wherein the nerve ganglia is a parasympathetic nerve ganglia. In some embodiments, the nerve ganglia is a sphenopalatine ganglia, a ciliary ganglia, a submandibular ganglia, superior cervical ganglia, trigeminal ganglia, stellate ganglia and/or an otic ganglia. In other instances, the nerve ganglia is a sphenopalatine ganglia. In yet other embodiments, the botulinum neurotoxin is applied to a pterygopalatine fossa. In still other embodiments, the botulinum neurotoxin is applied to the sphenopalatine ganglia. In yet other embodiments, the botulinum neurotoxin is applied zygomatically, intranasally, through a hard palate technique, using a high tuberosity approach or combinations thereof.

In some embodiments, the skin disorder is chosen from the group consisting of acne, eczema, psoriasis, seborrhea, rosacea and combinations thereof In still other instances, the botulinum neurotoxin is chosen from the group consisting of botulinum neurotoxin type A, botulinum neurotoxin type B, botulinum neurotoxin type C, botulinum neurotoxin type D, botulinum neurotoxin type E, botulinum neurotoxin type F, botulinum neurotoxin type G, and combinations thereof. In some instances, the botulinum neurotoxin type B is administered with epinephrine. In still other instances, the botulinum neurotoxin type B further comprises a basic solution. In other instances, the amount of botulinum neurotoxin administered is between about 0.1 to about 1000 units. In yet other instances, the amount of botulinum neurotoxin administered is between about 5 to about 50 units. In still other embodiments, the botulinum neurotoxin is administered over a period of time. In yet other embodiments, the botulinum neurotoxin is administered over one minute. In still other instances, the volume of botulinum neurotoxin administered is between 0.1 to 10 cc. In yet other embodiments, the botulinum neurotoxin is further administered locally to the skin.

Disclosed herein are methods and compositions of smoothing skin and reducing wrinkles in skin, the method comprising applying a therapeutically effective amount of botulinum neurotoxin to nerve ganglia. In some embodiments, the skin pore size is reduced. In some instances, the botulinum neurotoxin is chosen from the group consisting of botulinum neurotoxin type A, botulinum neurotoxin type B, botulinum neurotoxin type C, botulinum neurotoxin type D, botulinum neurotoxin type E, botulinum neurotoxin type F, botulinum neurotoxin type G, and combinations thereof In yet other instances, the botulinum neurotoxin type B is administered with epinephrine. In still other instances, the botulinum neurotoxin type B further comprises a basic solution.

Disclosed herein are methods and compositions for treating skin infections related to excessive holocrine secretions comprising applying a therapeutically effective amount of botulinum neurotoxin to nerve ganglia. In some embodiments, the excessive holocrine secretion condition is chosen from the group consisting of hidradenitis, furuncles, carbuncles, styes, chalazions, horoleum and combinations thereof. In some embodiments, the botulinum neurotoxin is chosen from the group consisting of botulinum neurotoxin type A, botulinum neurotoxin type B, botulinum neurotoxin type C, botulinum neurotoxin type D, botulinum neurotoxin type E, botulinum neurotoxin type F, botulinum neurotoxin type G, and combinations thereof. In some embodiments, the botulinum neurotoxin type B is administered with epinephrine. In still other embodiments, the botulinum neurotoxin type B further comprises a basic solution.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

It has been unexpectedly found that botulinum neurotoxin (BoNT) can decrease the severity of numerous skin disorders by application to nerve ganglia including but not limited to the parasympathetic, sympathetic, and sensory ganglia. Accordingly, disclosed herein are methods and compositions for the treatment of skin disorders and diseases by application of a therapeutically effective amount of botulinum neurotoxin to nerve ganglia, including the following diseases and all their related forms: acne, eczema, psoriasis, rosacea and diseases related to excess holocrine and sebaceous disorders: seborrheic dermatitis, rhinophyma, and sebaceous cysts. Also disclosed herein are methods and compositions for the treatment of infectious conditions in the skin related to excessive holocrine secretions include hidradenitis, furuncles, carbuncles, styes, chalazions and horboleum by application to nerve ganglia of a therapeutically effective amount of botulinum neurotoxin. In addition, the application of botulinum neurotoxin to nerve ganglia can cause skin to become smooth, and thus to decrease wrinkling or the appearance of wrinkles in the skin.

Investigators have in the past applied botulinum neurotoxin to treat various diseases, including as a topical agent to the skin, but none have applied botulinum neurotoxin to nerve ganglia for the treatment of skin disorders and diseases.

For example, in 1994 Sanders and Shaari (U.S. Pat. No. 5,766,605, Treatment of autonomic nerve dysfunction with botulinum toxin) discovered that BoNT could be used to treat disorders of the autonomic nerves. Indications included rhinorrhea, asthma, and decreasing sweating (hyperhidrosis). In 1995, Binder discovered that injection of BoNT into the mid face for cosmetic purposes also had a beneficial effect on psoriasis, dermatitis, and forms of pityriasis (U.S.

Pat. No. 5,670,484A Method for treatment of skin lesions associated with cutaneous cell-proliferative disorders). The mechanism of this improvement was unknown, however, Binder theorized that these diseases resulted from excessive growth of skin cells. The BoNT somehow decreased the production of new skin cells.

In 2001, Suskind et al. (U.S. Pat. No. 7,226,605B2 Botulinum toxin in the treatment or prevention of acne) discovered that injections of botulinum toxin can decrease the severity of acne vulgaris. In 2002, Sanders and Aquila discovered that application of botulinum toxin to the skin can decrease sebaceous secretions, thereby treating seborrhea. Unexpectedly, they also found that botulinum toxin decreased rosacea. Moreover, they also discovered that there were cosmetic benefits of BoNT, specifically smoothing of skin and decrease in fine wrinkles. See U.S. Pat. No. 7,288,259 (Treatment of holocrine gland dysfunction with clostridia neurotoxin); U.S. Pat. No. 8,202,522 (Skin cosmesis treatment with clostridia neurotoxins).

In 2002, Sanders discovered that application of BoNT to the nose or sphenopalatine ganglion (SPG) decreased all symptoms of allergic rhinitis (sneezing, itching, congestion and rhinorrhea) and asthma (U.S. Pat. Nos. 8,088,360, 9,314,513 8,092,781, 8,349,292, 7,879,340). In 2003, Sanders also discovered that botulinum toxin applied to the sphenopalatine ganglion could decrease migraine headaches (U.S. Pat. No. 9,504,735). More recently, Bratback et al. confirmed Dr. Sanders' findings by showing that 25 units of botulinum toxin applied bilaterally to the PPF and SPG can cause a 50% decrease in migraine headaches, and a similar decrease in the number of cluster headaches.

Migraine is thought to be a disease caused by dilation of cerebral blood vessels. In animal studies, perivascular fibres of intracranial arteries have been traced back to the SPG and stimulation of the SPG induces dilatation of cranial blood vessels, plasma protein extravasation and release of inflammatory substances. Activation of parasympathetic fibres traversing the SPG may be involved in migraine pathophysiology. In the SPG preganglionic parasympathetic fibres synapse with postganglionic fibres using acetylcholine as the neurotransmitter. BoNT causes neural block by inhibiting acetylcholine release and may therefore block parasympathetic signaling through the SPG and hence inhibit perivascular release of neurotransmitters involved in migraine. Since sympathetic and sensory fibres do not synapse in the sphenopalatine fossa, it seems reasonable to posit that synaptic transmission will not be affected. No event of numbness or paraesthesia distant from the injection site was registered. In both studies the author carefully chronicled all changes in the subjects, yet other than headache, the improvement in any symptoms and conditions mentioned above after application of local anesthetic to the SPG were not seen.

In skin disorders, however, the pathophysiology differs. One theory for acne proposes that a neuropeptide called substance P plays an important role. Substance P has been implicated in pain, inflammation, sebaceous secretions and epithelial hypertrophy. Many of these phenomena are seen in skin disorders. Substance P is not prominent in cholinergic parasympathetic neurons. Rather it is present in certain sensory neurons and a poorly understood class of neurons called non-adrenergic non-cholinergic.

In the head and neck there is a single sympathetic ganglion (superior cervical ganglia) and four parasympathetic ganglia ciliary, sphenopalatine, submandibular and otic. Each ganglion is associated with and attached to one of the cranial nerves. The superior sympathetic ganglia supplies all sympathetic innervation to the head. The four parasympathetic ganglia are: 1. The ciliary ganglion carries parasympathetic neurons with the 3rd cranial nerve (oculomotor) and supplies innervation to the orbit. 2. The sphenopalatine ganglia (SPG) carries parasympathetic neurons from the 7th cranial nerve (facial nerve) and lies under the second division (maxillary branch) of the 5th cranial nerve (trigeminal) in the pterygopalatine fossa (PPF). Among its functions it innervates a large area of the skin of the face. 3. The submandibular ganglia also carries parasympathetic neurons from the 7th cranial nerve (facial nerve) and is located beneath and lateral to the tongue. It controls the production of saliva from the submandibular and sublingual glands. 4. The otic ganglion carries parasympathetic neurons from the 9th cranial nerve (the glossopharyngeal) and hangs beneath the third division of the trigeminal nerve (mandibular branch). The otic ganglia innervates the skin in the lower face and neck.

Botulinum Neurotoxin

Botulinum toxins (BoNT) are potent poisons present in nature produced by the anaerobic bacterium *Clostridium botulinum* and *beratii*. Seven serotypes of toxins have been recognized, named as A through G. Recently, a novel toxin serotype was discovered and designated "H", although its identity is controversial. The active BTX molecule consists of two chains weighing ~150,000 Daltons, in which a heavy chain is linked by a disulfide bond to a light chain. Each chain has specific action; the former is responsible for neuron internalization, and the light chain binds to a specific target protein involved in the docking and fusion of acetylcholine-containing vesicles collectively referred to as the SNARE complex, which is responsible for vesicle acetylcholine release. BoNT-A cleaves a protein of the SNARE complex termed SNAP-25, blocking acetylcholine release. The derangement of this process at neuro-muscular junctions causes clinical effects consisting of muscle weakness and paralysis. To date, four formulations of BoNT-A are on the market and used in clinical practice: onabotulinumtoxinA (Botox, Allergan, Inc., Irvine, Calif., USA), abobotulinumtoxinA (Dysport, Ipsen Ltd., Berkshire, UK), incobotulinumtoxinA (Xeomin, Merz, Frankfurt, Germany), and a Chinese toxin Prosigne (Lanzhou Institute, Lanzhou, China). The preparations differ in the process of production, the formulations and the potencies which are determined by different biological assays based on their clinical use. BoNT-B classified as rimabotulinumtoxinB, is commercially available and marketed by Solstice Neuroscience (Malvern, Pa., USA) as MyoBloc in the United States and NeuroBloc (Elan Pharmaceuticals, San Diego, Calif., USA) in Europe. It is important to note that the potency of a single unit is variable among the commercial formulations. The potency of 1 U of onabotulinumtoxinA (Botox) is about equal to 1 U of incobotulinumtoxinA (Xeomin), 3 U of abobotulinumtoxinA (Dysport) and 40 to 50 U of rimabotulinumtoxinB (Neurobloc). However, it is very important to recognize that this ratio of equivalence cannot be employed. For injections, botulinum toxins type A are diluted with 0.9% sodium chloride solution.

(a) General Considerations for BoNT Injection or Topical Application.

Injections are preferably made every 3-12 months or upon return of symptoms. The dose injected on one side can vary from about 0.1-1000 units, preferably about 5-50 units, and more preferably about 20-30 units for botulinum neurotoxin type A, for example onabotulinumtoxin A (Botox). In some instances and depending upon the type of botulinum neurotoxin used, the amount employed would increase, for example, for rimbotulinumtoxin B (Neurobloc) the amount administered would be approximately 50-times the amount of botulinum neurotoxin relative to onabotulinum toxin A (botox), i.e., from about 5-50,000 units, preferably about 250-2500 units, and more preferably about 1000-1500 units for botulinum neurotoxin type B. Injections can be unilateral or bilateral depending on the nature and location of the lesion. Injections can be done simultaneously on both sides or separately.

In another embodiment of this technique, an injection of epinephrine can precede, or be given simultaneous or even after the BoNT injection. The epinephrine contracts blood vessels, thereby decreasing the soft tissue volume within the pterygopalatine fossa. It also aids in preventing or minimizing any bleeding in the fossa. In addition, it decreases the extracellular space and fluid exchange in the area, decreasing the spread of the toxin.

In another embodiment the local and systemic spread of toxin can be minimize, a non-limiting example being serotype B a used. Type B is marketed in liquid form with preservation aided by an acidic pH of 5.6. This particular product is known for its pain on injection and for seemingly substantial systemic spread to autonomically innervated structures, a non-limiting example being the salivary glands which decreases salivation which the patient experiences as dry mouth. To combat these side effects, the type B BoNT solution may be combined with epinephrine described above. In the particular case of BoNT the acidic nature of the solution may cause inflammation with increased fluid release and uptake by local blood vessels. This increased fluid exchange could remove BoNT type B from the area and allow it to enter the systemic circulation. To minimize this, a basic solution to neutralize the acid pH and decrease the acidic nature of the injection. This decreases pain and the inflammation in the area.

The devised volumes are variable and depend on the planned dose that the clinician intends to inject. As it is preferable that the injection be localized to thee target, small volumes of injection solution are preferable (0.1 to 10 cc, preferably 0.5 to 1 cc). It is also preferable that the BoNT is injected slowly, including about 10 seconds to hours, in some instances about 30 seconds to about an hour, in yet other instances about 30 seconds to about 10 minutes, in still other instances about 1 minute to about 5 minutes, preferably 1 minute. Long injections are possible by computer-controlled injection needles.

Depending on the experience of the physician and other factors, injections can be done with the physician using navigation aids in needle placement. In intra nasal injection a rigid endoscope provides direct visualization of the injection site, and/or the site for topical mucosal application. Ct scans and or MRI imaging can be obtained to see the anatomy of a proposed injection site in or to plan the injection route. Using CT scans a 3 dimensional model of the bony injection site can be made. Then the physician can plan exactly what injection parameters he needs. A 3 dimensional guide could be manufactured to aid the physician.

BoNT toxin can be injected to various targets with or without local medication. The type of BoNT can differ, a non-limiting example being that BoNT type E, a short acting toxin that may be used to test the response of a skin lesion, or to provide temporary relief when some symptoms flare up intermittently. These injections can be separated in time. Injection of each side can be done simultaneously, or the injections may separated in time from days to months.

BoNT and other medications may be applied in various combinations. As a non-limiting example, the SPG can be injected by itself on one side, both sides, with another ganglia injection, and with a local application of BoNT or other medication to the lesions on the skin itself (topically, sub or intradermal). Non-limiting example of combinations of therapy may include BoNT to the ganglia with or without local medication, different BoNT preparations at various sites, BoNT and local medication at the lesion site, systemic medication with or without BoNT or local medications. Electrical stimulation can be used to help navigation. The tip of the needle may have a monopolar or bipolar electrode. As the needle approaches the SPG the subject feels sensation in the base of his nose and the medication is injected. Those familiar with clinical practice art can readily envision variations on drug therapies known in the art.

(b) Sphenopalatine (SPG) Ganglia

The SPG is a non-limiting example of a ganglia. It is located in the pterygopalatine fossa (PPF) deep in the skull behind the maxillary sinus. Within the PPF the trigeminal nerve passes through supplying sensory neurons to the face, sympathetic neurons pass through, and parasympathetic neurons synapse to their post ganglionic neurons which are distributed throughout the head and neck.

BoNT can be applied by injection to the SPG ganglia in four different ways (i) Zygomatic In the suprazygomatic approach the patient is placed supine with the head in a neutral position. The needle entry point is found at the angle formed by the superior edge of the zygomatic arch below and the posterior orbital rim forward. The needle (22 to 25 gauge) is inserted perpendicular to the skin and advanced to reach the greater wing of the sphenoid at a depth of approximately 10-15 mm). The needle is then reoriented in a caudal and posterior direction and advanced a further 35-45 mm to reach the pterygopalatine fossa. After a negative aspiration test for blood, solution is slowly injected. Nerve stimulation may help locate the pterygopalatine fossa: Nerve stimulation is associated with paresthesia coinciding with the stimulating frequency of the nerve stimulator. In anesthetized children, stimulation of the temporal muscle that results in a mandibular contraction may be noted. The disappearance of the muscle contraction heralds the passage through the temporal muscle and entrance into the pterygomaxillary fossa. In an alternative embodiment the needle can be inserted below the zygomatic arch (infrazygomatic).

(ii) Intranasal

Preferably the nose is decongested with phenylephrine or epinephrine and anesthetized with lidocaine. A flexible or rigid scope is passed into the nasal cavity such that it visualizes the mucosa posterior to the middle turbinate. A syringe contained BoNT diluted with preferably 1-4 cc of normal saline is attached to a long needle preferably about 3.5 cm and preferably 27 gauge. The needle is introduced into the nasal cavity and advanced until the needle tip is at the posterior border of the middle turbinate. The needle is then slowly advanced 1-10 mm through mucosa behind the middle turbinate. The needle is aspirated and then injection is made.

Topical intranasal administration may be done by saturating a cotton pledgets or other porous material and placing it into the nose such that it lies against nasal mucosa. A cotton applicator or similar device can be used to deliver more localized medication.

(iii) Palatal

The patient is placed supine and asked to open the mouth widely. The exit of the pterygopalatine canal is identified on the hard palate about mid-way between the $2^{nd}$ or $3^{rd}$ molar and the midline. A needle is advanced into the foramen in a posterosuperior direction at an angle of 45-60 degrees from the horizontal plane of the hard palate. At 20-30 mm the needle is aspirated and then injection is made.

(iv) High Tuberosity

A 25-gauge long needle is recommended for this injection, but a 27-gauge is acceptable. The penetration site for the maxillary block is the height of the mucobuccal fold distal to the maxillary second molar. Prior to placing topical anesthetic, it is important to use a finger to feel along the facial aspect of the maxilla to find the zygomatic process, which is usually located above the first maxillary molar. It is important to insert distal to the zygomatic process or the maxillary bone may be scraped during administration. The angle of the syringe should be 45° from the mid-sagittal plane, as well as 45° apically from the maxillary occlusal plane. A helpful visual guide for this angle is a line running from the lateral periphery of the ala of the nose to the inside corner of the opposite eyebrow. The average depth of penetration for the maxillary block is 30 mm. With a 32 mm long needle, 2 mm of needle should remain visible outside the tissue. The bone should not be contacted on this injection, and the needle should progress smoothly through the tissues. The clinician should know the exact length of the needle, as different manufacturers produce different needle lengths. If both aspirations are negative, the injection anesthetic should be slowly deposited, re-aspirating every ¼ of the cartridge to make sure a blood vessel has not been penetrated. The clinician should administer this injection slowly (taking more than 60 seconds to deliver the full amount) because of the highly vascular nature of the pterygopalatine fossa.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Treatment of Acne (i) 1A, Hard Palate Technique (Greater Palatine or Pterygopalatine Canal).

A 16 year old girl has acne with continual blockheads on both cheeks with flareups of acne vulgaris with papules on her forehead and cheeks. Her physician reconstitutes 100 units BoNT with 4 cc of normal saline. The physician injects her SPG with 1 cc of solution using the palatal technique. The exit of the pterygopalatine canal is identified on the hard palate about mid-way between the $2^{nd}$ or $3^{rd}$ molar and the midline. A cotton tip applicator with 4% lidocaine is applied to the mucosa overlying the entrance of the pterygopalatine canal for 3 minutes. A needle is advanced into the foramen in a posterosuperior direction at an angle of 45-60 degrees from the horizontal plane of the hard palate. At 20-30 mm the needle is aspirated and then injection of 1 cc (25 units) is made. The result is a 50% improvement in papule numbers and size within 2 weeks.

(ii) 1B. Zygomatic Techniques

In another embodiment, the same patient described in 1A above is injected using the suprazygomatic approach. The patient is placed supine with the head in a neutral position. The needle entry point is found at the angle formed by the superior edge of the zygomatic arch below and the posterior orbital rim forward. The needle (22 to 25 gauge) is inserted perpendicular to the skin and advanced to reach the greater wing of the sphenoid at a depth of approximately 10-15 mm). The needle is then reoriented in a caudal and posterior direction and advanced a further 35-45 mm to reach the pterygopalatine fossa. After a negative aspiration test for blood, solution is slowly injected. Nerve stimulation may help locate the pterygopalatine fossa: Nerve stimulation is associated with paresthesia coinciding with the stimulating frequency of the nerve stimulator. In anesthetized children, stimulation of the temporal muscle that results in a mandibular contraction may be noted. The disappearance of the muscle contraction heralds the passage through the temporal muscle and entrance into the pterygomaxillary fossa.

In another embodiment the procedure is performed under x-ray visualization (Fluoroscopy). In this technique an x-ray machine can provide real time continuous x-ray images of the bony skull. The needle tip can then be visualized to be in the proper position prior to injection.

In an alternative embodiment the needle can be inserted below the zygomatic arch (infrazygomatic approach). In this technique the needle is inserted underneath the zygomatic arch.

(iii) 1C. High Tuberosity Approach.

In another embodiment the high tuberosity method is used. A 25-gauge long needle is recommended for this injection, but a 27-gauge is acceptable. The penetration site for the maxillary block is the between the upper lip and the upper maxillary teeth. Prior to placing topical anesthetic, it is important to use a finger to feel along the facial aspect of the maxilla to find the zygomatic process, which is usually located above the first maxillary molar. It is important to insert distal to the zygomatic process or the maxillary bone may be scraped during administration. The angle of the syringe should be 45° from the mid-sagittal plane, as well as 45° apically from the maxillary occlusal plane. A helpful visual guide for this angle is a line running from the lateral periphery of the ala of the nose to the inside corner of the opposite eyebrow. The average depth of penetration for the maxillary block is 30 mm. With a 32 mm long needle, 2 mm of needle should remain visible outside the tissue. The bone should not be contacted on this injection, and the needle should progress smoothly through the tissues. The clinician should know the exact length of the needle, as different manufacturers produce different needle lengths. If both aspirations are negative, the injection anesthetic should be slowly deposited, re-aspirating every ¼ of the cartridge to make sure a blood vessel has not been penetrated. The clinician should administer this injection slowly (taking more than 60 seconds to deliver the full amount) because of the highly vascular nature of the pterygopalatine fossa.

(iv) 1D. Intranasal

The patient lies with the side of the head to be injected horizontal to the floor. If decongestion or anesthesia is needed, 1% lidocaine with epinephrine 1:100,000 is applied. 1-4 cc are placed on a cotton pledget that is placed into the nasal cavity for 15 minutes, or one or both medication can also be sprayed. After decongestion and anesthesia is obtained a 2-5 mm rigid or flexible endoscope is placed into the nostril and advanced backward to visualize the nasal cavity. A 5 inch needle with a ¼ inch curve is inserted into the nasal cavity and advance into the nasal cavity. The tip of the needle is then seen by the endoscope. The needle then is pushed through the mucosa over the sphenopalatine foramen and the advanced 5-10 mm further. A 0.5 cc solution of 50 units BoNT is slowly injected over 2 minutes. After injection the patient is instructed to lie in the same position for an additional 30 minutes.

In another embodiment the 50 nits of BoNT solution is saturate onto a cotton applicator. With a scope in place the applicator is advanced slowly backward in the nose until reaching the area behind the middle turbinate. The applicator is placed against the mucosa for 1 hour.

(v) 1E. Combined Therapy

The patient experiences a flare up of her acne despite being one month after her botulinum neurotoxin injection. The physician notes bilateral blackheads on on both cheeks with some cystic lesions He diagnoses comedone acne with an acne vulgaris component. A course of topical Tretinoin cream 0.05% is prescribed to be applied twice a day to the affected area. In addition, a ten day course of the antibiotic oral tetracycline is prescribed. After two weeks most of the comedone have disappeared but there is only a 50% improvement in thee acne vulgaris cystic lessons. The physician then injects 0.1 c of a 1 cc solution containing 100 units of BoNT. Each injection is made intradermally directly next to a cystic lesion. After 2 weeks the patient has complete resolution of her acne vulgaris. Due to the good response to intradermal BoNT she is placed on a regimen of intradermal injections every 3 months with oral and topical medications added during flareups.

Example 2: Eczema

A 40-year-old female has eczema on her scalp. Her physician reconstitutes 100 units in 2 ccc of normal saline. The nose is decongested with 1:100,000 phenylephrine or epinephrine and anesthetized with 1% lidocaine. A flexible or rigid scope is passed into the nasal cavity such that it visualizes the mucosa posterior to the middle turbinate. A syringe contained BoNT diluted with 1 cc of normal saline is attached to a long needle preferably about 3.5 cm and preferably 27 gauge. The needle is introduced into the nasal cavity and advanced until the needle tip is at the posterior border of the middle turbinate. The needle is then slowly advanced 5 mm through mucosa behind the middle turbinate. The needle is aspirated and then a 0.25 cc injection is made slowly over 1 minute. When seen in 1 week the eczema has completely resolved.

Example 3: Seborrhea

All variations of seborrhea diseases as described above are alternative embodiments: seborrheic dermatitis, rhinophyma, and sebaceous cysts. Infectious conditions related to excessive holocrine secretions include hidradenitis, furuncles, carbuncles, styes, chalazions and horboleum.

A 40-year-old male has seborrheic dermatitis on his scalp. His physician reconstitutes 100 units in 2 cc of normal saline. The nose is decongested with 1:100,000 phenylephrine or epinephrine and anesthetized with 1% lidocaine. A flexible or rigid scope is passed into the nasal cavity such that it visualizes the mucosa posterior to the middle turbinate. A syringe contained BoNT diluted with 1 cc of normal saline is attached to a long needle preferably about 3.5 cm and preferably 27 gauge. The needle is introduced into the nasal cavity and advanced until the needle tip is at the posterior border of the middle turbinate. The needle is then slowly advanced 5 mm through mucosa behind the middle turbinate. The needle is aspirated and then a 0.25 cc injection is made slowly over 1 minute. When seen in 1 week the seborrheic dermatitis has completely resolved.

Example 4: Psoriasis

A 30-year-old female has a 4 cm×6 cm patch of psoriasis on the back of her neck. Her physician reconstitutes 100 units of Dysport with 2 cc of normal saline and is drawn into a 5-cc syringe. A 25-gauge 3.5-inch needle is attached to the syringe. Using his finger the facial aspect of the maxilla is palpated to find the zygomatic process, the needle is then inserted distal to the zygomatic process. The needle is introduced into the mucobuccal fold distal to the maxillary second molar. The angle of the syringe should be 45° from the mid-sagittal plane, as well as 45° apically from the maxillary occlusal plane. A helpful visual guide for this angle is a line running from the lateral periphery of the ala of the nose to the inside corner of the opposite eyebrow. The average depth of penetration for the maxillary block is 30 mm. With a 32 mm long needle, 2 mm of needle should remain visible outside the tissue. The bone should not be contacted on this injection, and the needle should progress smoothly through the tissues. If aspirations are negative, the injection of 1 cc (50 units) should be slowly deposited, re-aspirating every ¼ of the cartridge to make sure a blood vessel has not been penetrated. The clinician should administer this injection slowly (taking more than 60 seconds to deliver the full amount) because of the highly vascular nature of the pterygopalatine fossa. Injection is then made to the opposite side. When seen by the physician at 1 week the psoriasis lesion has shrunk by 50%, then 80% by the second week. The effect lasts for 1 year.

Example 5: Rosacea

A 40-year-old male has a rosacea involving both cheeks. The physician reconstitutes 100 units of Botox with 4 cc of normal saline. The exit of the pterygopalatine canal is identified on the hard palate about mid-way between the $2^{nd}$ or $3^{rd}$ molar and the midline. A needle is advanced into the foramen in a posterosuperior direction at an angle of 45-60 degrees from the horizontal plane of the hard palate. At 20-30 mm the needle is aspirated and then injection is made over 1 minute. A second injection is made on the opposite side. The rosacea completely resolves over 1 month.

Example 6: Skin Smoothing 60 year old female is concerned by the rough texture, large skin pores and wrinkles of her facial skin. Her physician reconstitutes 100 units of Xeomin in 2 cc of normal saline. The nose is decongested with 1:100,000 phenylephrine or epinephrine and anesthetized with 1% lidocaine. A flexible or rigid scope is passed into the nasal cavity such that it visualizes the mucosa posterior to the middle turbinate. A syringe contained BoNT diluted with 1 cc of normal saline is attached to a long needle preferably about 5 cm and preferably 27 gauge. The needle is introduced into the nasal cavity and advanced until the needle tip is at the posterior border of the middle turbinate. The needle is then slowly advanced 5 mm through mucosa behind the middle turbinate. The needle is aspirated and then a 1 cc injection is made slowly over 1 minute. Then the opposite side is injected with the same amount. When seen in 1 month the skin is notable smoother with smaller skin pores and has less prominent wrinkling.

Example 7: Oily Skin

A 40 year old female complains of oily skin which she finds socially unacceptable. She does not want multiple injections into her face. The physician lies the patient supine and anesthetizeds the mucosa above the foramen with topical anesthetic. After 2 minutes he inserts a 30 mm 29 gauge needle through the greater palatine canal to a depth of 25 mm and injects 0.5 cc of a solution containing 25 units of BoNT. The same injection is repeated on the opposite side. The patient is instructed to remain in the same position for 30 minutes. One week later the patient returns and reports that her oily skin problem has resolved.

Bratbak D F, Nordgård S, Stovner L J, Linde M, Dodick D W, Aschehoug, Folvik, Tronvik E. Pilot study of sphenopalatine injection of onabotulinumtoxinA for the treatment of intractable chronic migraine. Cephalalgia. 2017 April; 37(4):356-364. doi: 10.1177/0333102416648328. Epub 2016 May 6.

Bratbak DF1, Nordgård S2, Stovner LJ3, Linde M4, Folvik M5, Bugten V2, Tronvik E4. Cephalalgia. Pilot study of sphenopalatine injection of onabotulinumtoxinA for the treatment of intractable chronic cluster headache. 2016 May; 36(6):503-9. doi: 10.1177/0333102415597891. Epub 2015 Jul. 31

DasGupta, B. R. Structures of botulinum neurotoxin, its functional domains and perspectives on the crystalline tipe A toxin. In Therapy with Botulinum Toxin; Jankovic, J., Hallet, M., Eds.; Marcel Dekker: New York, N.Y., USA, 1994; pp. 15-39.

Dressler, D. Routine use of Xeomin in patients previously treated with Botox: Long term results. Eur. J. Neurol. 2009, 16 (Suppl. S2), 2-5

Schiavo, G.; Benfenati, F.; Poulain, B.; Rossetto, O.; Polverino de Laureto, P.; DasGupta, B. R.; Montecucco, C. Tetanus and boulinum-B neurotoxin block neurotransmitter release by a proteolytic cleavage of synapto-brevin. Nature 1992, 359, 832-835.

Benecke, R.; Jost, W. H.; Kanovsky, P.; Ruzicka, E.; Comes, G.; Grafe, S. A new botulinum toxin type A free of complexing proteins for treatment of cervical dystonia. Neurology 2005, 64, 1949-1951.

Dressler, D. Routine use of Xeomin in patients previously treated with Botox: Long term results. Eur. J. Neurol. 2009, 16 (Suppl. S2), 2-5

Malamed S. Handbook of Local Anesthesia. 6th ed. St. Louis: Elsevier Mosby; 2013

Malamed S. Handbook of Local Anesthesia. 6th ed. St. Louis: Elsevier Mosby; 2013

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating skin disorders comprising applying a therapeutically effective amount of botulinum neurotoxin to nerve ganglia.

2. The method of claim 1, wherein the nerve ganglia is a parasympathetic nerve ganglia.

3. The method of claim 1, wherein the nerve ganglia is a sphenopalatine ganglia, a ciliary ganglia, a submandibular ganglia, superior cervical ganglia, trigeminal ganglia, stellate ganglia and/or an otic ganglia.

4. The method of claim 1, wherein the nerve ganglia is a sphenopalatine ganglia.

5. The method of claim 4, wherein the botulinum neurotoxin is applied to a pterygopalatine fossa.

6. The method of claim 1, wherein the botulinum neurotoxin is applied to the sphenopalatine ganglia.

7. The method of claim 6, wherein the botulinum neurotoxin is applied zygomatically, intranasally, through a hard palate technique, using a high tuberosity approach or combinations thereof.

8. The method of claim 1, wherein the skin disorder is selected from the group consisting of acne, eczema, psoriasis, seborrhea, rosacea and combinations thereof.

9. The method of claim 1, wherein the botulinum neurotoxin is selected from the group consisting of botulinum neurotoxin type A, botulinum neurotoxin type B, botulinum neurotoxin type C, botulinum neurotoxin type D, botulinum neurotoxin type E, botulinum neurotoxin type F, botulinum neurotoxin type G, and combinations thereof.

10. The method of claim 1, wherein the botulinum neurotoxin is botulinum neurotoxin type A.

11. The method of claim 1, wherein the botulinum neurotoxin is botulinum neurotoxin type B.

12. The method of claim 11, wherein the botulinum neurotoxin type B is administered with epinephrine.

13. The method of claim 11, wherein the botulinum neurotoxin type B further comprises a basic solution.

14. The method of claim 1, wherein the amount of botulinum neurotoxin administered is between about 0.1 to about 1000 units.

15. The method of claim 1, wherein the amount of botulinum neurotoxin administered is between about 5 to about 50 units.

16. The method of claim 1, wherein the botulinum neurotoxin is administered over a period of time.

17. The method of claim 1, wherein the botulinum neurotoxin is administered over one minute.

18. The method of claim 1, wherein the volume of botulinum neurotoxin administered is between 0.1 to 10 cc.

19. The method of claim 1, wherein the botulinum neurotoxin is further administered locally to the skin.

* * * * *